United States Patent
Wong et al.

[11] Patent Number: 5,804,048
[45] Date of Patent: Sep. 8, 1998

[54] ELECTRODE ASSEMBLY FOR ASSAYING GLUCOSE

[75] Inventors: David K. Wong, Del Mar; Joseph Y. Lucisano, San Diego, both of Calif.

[73] Assignee: Via Medical Corporation, San Diego, Calif.

[21] Appl. No.: 698,045

[22] Filed: Aug. 15, 1996

[51] Int. Cl.$^6$ .............................. G01N 27/26; C12Q 1/00
[52] U.S. Cl. .......................... 204/403; 205/778; 435/817
[58] Field of Search ...................... 156/273.9; 427/2.11, 427/2.12, 2.13, 58; 204/403; 205/778, 72, 793; 438/817

[56] References Cited

U.S. PATENT DOCUMENTS

| | | | |
|---|---|---|---|
| 3,542,662 | 11/1970 | Hicks et al. | 204/403 |
| 3,791,933 | 2/1974 | Moyer et al. | 195/127 |
| 3,948,745 | 4/1976 | Guilbault et al. | 204/195 B |
| 3,979,274 | 9/1976 | Newman | 204/195 B |
| 4,073,713 | 2/1978 | Newman | 204/403 |
| 4,201,088 | 5/1980 | Trietley, Jr. | 73/342 |
| 4,220,503 | 9/1980 | Johnson | 204/1 T |
| 4,307,195 | 12/1981 | Karasawa et al. | 435/288 |
| 4,317,879 | 3/1982 | Busby et al. | 435/14 |
| 4,356,074 | 10/1982 | Johnson | 204/195 P |
| 4,388,166 | 6/1983 | Suzuki et al. | 204/403 |
| 4,404,066 | 9/1983 | Johnson | 204/1 T |
| 4,415,666 | 11/1983 | D'Orazio et al. | 435/179 |
| 4,484,987 | 11/1984 | Gough | 204/1 T |
| 4,650,547 | 3/1987 | Gough | 204/1 T |
| 4,704,029 | 11/1987 | Van Heuvelen | 356/39 |
| 4,757,022 | 7/1988 | Shults et al. | 435/291 |
| 4,759,828 | 7/1988 | Young et al. | 204/1 T |
| 4,764,879 | 8/1988 | Campbell | 364/482 |
| 4,832,797 | 5/1989 | Vadgama et al. | 205/778 |
| 5,034,330 | 7/1991 | Yamori et al. | 435/288 |
| 5,217,595 | 6/1993 | Smith et al. | 204/412 |
| 5,254,235 | 10/1993 | Wu | 204/284 |
| 5,298,144 | 3/1994 | Spokane | 204/403 |
| 5,429,726 | 7/1995 | Johnson et al. | 204/153.12 |
| 5,520,788 | 5/1996 | Johnson | 205/415 |
| 5,624,537 | 4/1997 | Turner et al. | 204/403 |

FOREIGN PATENT DOCUMENTS

0216577  4/1987  European Pat. Off. .

*Primary Examiner*—Kathryn L. Gorgos
*Assistant Examiner*—Alexander Noguerola
*Attorney, Agent, or Firm*—Sheppard, Mullin Richter & Hampton LLP

[57] ABSTRACT

An improved electrode assembly is disclosed for use in assaying glucose in solution, e.g., in undiluted whole blood. The assembly includes a sensor electrode and a special overlaying multi-layer membrane that can be sterilized by gamma radiation without reducing the activity of a glucose oxidase enzyme located in an intermediate layer of the membrane. An outer layer of the membrane is formed with microscopic pores having a predetermined density and predetermined size, for reliably controlling the flux of glucose and oxygen from the solution to the intermediate layer, where they react in the presence of the glucose oxidase enzyme to form reactions products that include hydrogen peroxide. The outer layer thus functions as a diffusion barrier, to eliminate the adverse effects of any oxygen deficit that might be present. In addition, an inner layer of the membrane functions as an interference barrier, for controlling the permeation of the hydrogen peroxide reaction product to the underlying electrode. The inner layer includes a relatively thick, porous backing film, formed for example of porous polyester, and a relatively thin, porous overlaying film, formed for example of polysulfone.

17 Claims, 2 Drawing Sheets

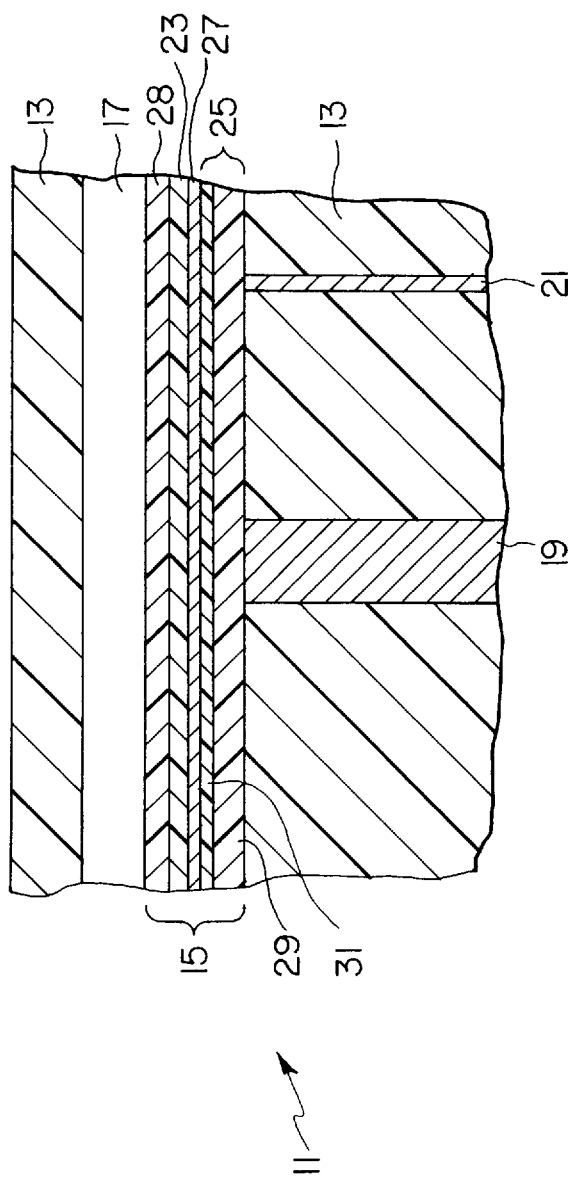

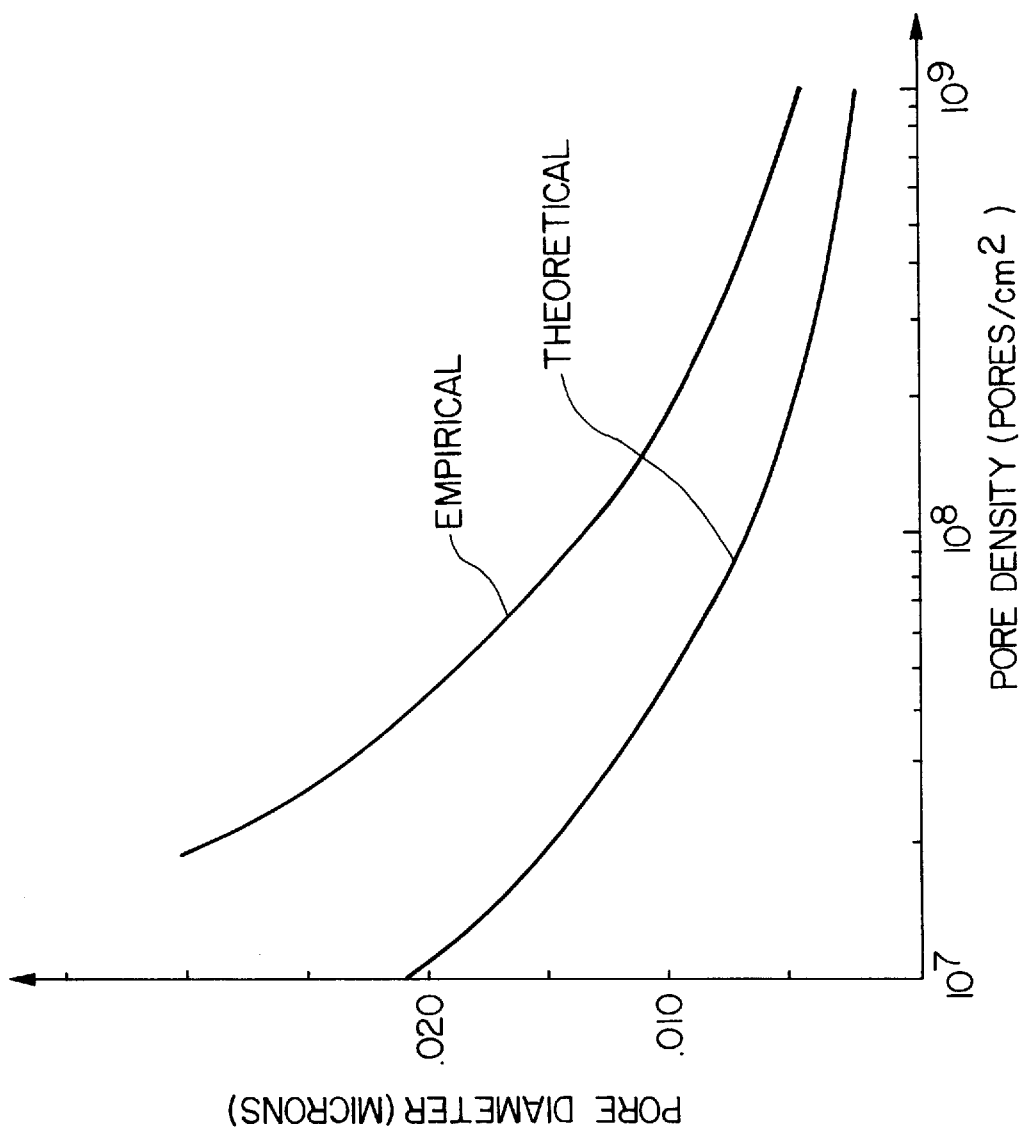

ELECTRODE ASSEMBLY FOR ASSAYING GLUCOSE

BACKGROUND OF THE INVENTION

This invention relates generally to electrode assemblies for use in assaying glucose in solution and, more particularly, to electrode assemblies incorporating a glucose oxidase membrane.

Electrode assemblies of this particular kind typically include a polarographic electrode overlaid by a special membrane that incorporates the enzyme glucose oxidase. In use, the membrane is exposed to a sample solution to be assayed, e.g., undiluted whole blood, whereupon glucose, water and oxygen from the solution react together in the presence of the glucose oxidase catalyst, to produce gluconic acid and hydrogen peroxide. An electrical current is produced in accordance with the amount of hydrogen peroxide, and this current can be appropriately processed to produce a measurement of glucose concentration in the sample solution.

The glucose oxidase membrane typically includes several layers, with the glucose oxidase enzyme immobilized in a intermediate layer sandwiched between an outer layer that contacts the solution to be assayed and an inner layer that contacts the polarographic electrode. The outer layer functions as a diffusion barrier, allowing a substantially greater flux of oxygen than glucose to diffuse through it from the solution to reach the glucose oxidase layer. This is desired because the glucose oxidase enzyme reaction consumes equimolar quantities of glucose and oxygen, and the outer layer thus prevents the relatively lower concentration of oxygen in the solution from being the limiting factor in the assay.

The inner layer functions as an interference barrier, allowing the permeation of hydrogen peroxide to the underlying electrode, but blocking the permeation of other low molecular weight molecules, such as acetaminophen, ascorbic acid, uric acid, salicylic acid, and amino acids. Such other molecules could contribute to the generation of an electrical current.

The electrode assembly described briefly above has functioned generally satisfactorily in assaying glucose in solutions such as undiluted whole blood. Difficulty has arisen, however, in controlling the permeability of the outer, diffusion-barrier layer. One prior assembly, for example, has called for the outer layer to include pores having diameters in the range of 0.0010 to 0.0125 microns. However, the layer's permeability to glucose has been found to vary significantly according to the actual size, density and distribution of those pores, even if they all lie within the specified range. Another drawback to prior electrode assemblies of this kind is that the inner, interference-barrier layer has been so thin, typically merely several microns or less, that it has been difficult and costly to manufacture and has been difficult to handle.

Another drawback to prior electrode assemblies of this kind is that they are not believed to have been readily sterilizable using conventional gamma radiation. Such gamma radiation is believed to have denatured the functional groups of the glucose oxidase used in prior assemblies, rendering the assemblies ineffective.

It should, therefore, be appreciated that there is a need for an improved electrode assembly for use in accurately and reliably assaying glucose in a solution such as undiluted whole blood, which is not susceptible to difficulties in forming an outer, diffusion-barrier layer or an inner, interference-barrier layer, and which can withstand gamma radiation for purposes of sterilization without degradation. The present invention fulfills these and other needs.

SUMMARY OF THE INVENTION

The present invention is embodied in an electrode assembly, and a related method for manufacturing it, for use in assaying glucose in a solution, which can be sterilized by gamma radiation without losing its enzyme activity and which can be manufactured with reduced difficulty. The electrode assembly includes a sensor electrode and an overlaying multilayer membrane assembly. An outer layer of the membrane assembly is positioned to contact the solution to be assayed, and it functions as a diffusion barrier for controlling the flux of glucose and oxygen from the solution. In particular, the outer layer incorporates pores having a known distribution, e.g., random, and having a predetermined density and predetermined size in the range of 0.0125 to 0.020 microns. An inner layer of the membrane assembly contacts a face of the sensor electrode, and it functions as an interference barrier for reducing the permeation of undesirable species to the electrode. Finally, an immobilized glucose oxidase layer is interposed between the outer and inner layers, and it functions to facilitate an enzyme reaction between the glucose, water and oxygen that reach the layer from the solution. All three layers of the membrane assembly have predetermined, substantially uniform thicknesses.

The outer layer of the membrane assembly is configured to allow the diffusion of oxygen from the solution to a substantially greater degree than it allows the diffusion of glucose from the solution, e.g., by a factor of at least about 400. When the outer layer is formed of the preferred material polycarbonate, with a thickness of about 6 microns, the pores contribute about 0.003 percent to about 0.015 percent of the outer layer's total porosity.

In a separate and independent feature of the invention, the glucose oxidase layer of the membrane assembly incorporates albumin, which enables the membrane to be sterilized via gamma radiation, without degrading the enzyme activity of the glucose oxidase. This is an important advantage in some applications, such as where the solution being assayed is to be reinfused into a patient's blood vessel.

In another separate and independent feature of the invention, the inner layer of the membrane assembly includes a relatively thick, porous backing film and a relatively thin, porous overlaying film. The backing film can be formed of polyester, and the overlaying film can be formed of polysulfone. The backing film and overlaying film, together, have a combined thickness of about 15 microns.

Other features and advantages of the present invention should become apparent from the following description of the preferred embodiment, taken in conjunction with the accompanying drawings, which illustrate, by way of example, the principles of the invention.

BRIEF DESCRIPTION OF THE DRAWINGS

FIG. 1 is a cross-sectional drawing, not to scale, of an electrode assembly embodying the present invention, for assaying glucose in solution, the assembly incorporating a multi-layer glucose oxidase membrane.

FIG. 2 is a graph depicting the preferred relationship between pore size and pore density in the outermost layer of the glucose oxidase membrane of the electrode assembly of FIG. 1.

DESCRIPTION OF THE PREFERRED EMBODIMENT

With reference now to the drawings, and particularly to FIG. 1, there is shown an electrode assembly 11 configured for assaying glucose in a test solution such as undiluted whole blood. The assembly includes a molded plastic housing 13 that supports a multi-layer membrane 15 adjacent to a channel 17 that receives a blood sample. The membrane is configured to allow the diffusion into it of glucose, water and oxygen from the blood sample, which react together in the presence of the enzyme, glucose oxidase incorporated into the membrane, to produce gluconic acid and hydrogen peroxide. An electrical current thereby is generated between two electrodes 19 and 21 that underlay the membrane, the current varying according the concentration of hydrogen peroxide, and thus according to the concentration of glucose in the blood sample.

The multi-layer membrane 15 includes an outer diffusion-barrier layer 23, an inner interference-barrier layer 25, and an intermediate glucose oxidase layer 27 sandwiched between the outer and inner layers. Glucose, water and oxygen from the blood sample diffuse through the outer layer to reach the glucose oxidase layer. The resulting hydrogen peroxide reaction product permeates through the inner layer, to reach the electrodes 19 and 21 and provide carriers for an electrical current. An optional mechanical support layer 28 can be located adjacent to the outer layer 23.

The outer layer 23 of the multi-layer membrane 15 functions as a diffusion barrier, allowing a substantially greater proportion of glucose than oxygen to diffuse through it from the blood sample to reach the glucose oxidase layer 27. Preferably, the outer layer is at least about 400 times more permeable to oxygen than it is to glucose. This ensures that the concentration of glucose in the sample, and not the concentration of oxygen, is the limiting factor in the assay.

The outer layer 23 preferably has a thickness of about 6 microns, and it is formed of polycarbonate, which inherently is sufficiently porous to allow the permeation of oxygen from the blood sample in the channel 17 to the intermediate layer 27. In addition, the outer layer further is configured with a large number of randomly distributed cylindrical pores (not shown) extending completely through it, from the surface adjacent to the channel to the surface adjacent to the intermediate layer. The function of the pores is to diffuse glucose molecules from the channel to the intermediate layer. Glucose molecules otherwise are too large to permeate through the polycarbonate material.

The cross-sectional sizes of the pores formed in the outer layer 23 of the multi-layer membrane 15 are carefully controlled so as to provide the desired differentiation in diffusion between glucose and oxygen. In particular, the pore sizes are made to vary inversely with their density in the material. FIG. 2 is a graph showing both a theoretically derived relationship, and an empirically derived relationship, between pore density and pore size. For a pore density of about $1 \times 10_8$ pores per square centimeter, for example, a pore diameter of about 0.0135 microns is desired. The two parameters are related such that the pores contribute about 0.003 percent to about 0.015 percent to the material's total porosity.

The pores preferably are made to have diameters in the range of 0.0125 to 0.0200 microns. Pores of smaller size are considered too difficult to form with reliability, and pores of larger size would necessarily be spaced farther apart from each other, possibly leading to increased response times and possibly being subject to clogging by proteins or other relatively large molecules.

Thin-film, track-etched polycarbonate sheets in the specified thickness of 6 microns are available commercially in the form of rolls. The specified pores can be formed in such a roll by exposing them to radiation bombardment by heavy ions, for example using a particle accelerator, to produce weaknesses in the material, after which the roll is etched in a potassium hydroxide (KOH) bath. This process is described in greater detail in various materials published by Poretics Corp., of Livermore, Calif. Pore density is controlled according to the material's distance from the ion source and the speed at which the material is moved past the ion source. Pore size is controlled according to the temperature of the KOH bath and the material's dwell time in it.

The inner layer 25 of the multi-layer membrane 15 actually is a composite of two separate layers, i.e., a backing film 29 and an overlay film 31. This composite layer functions as an interference barrier that allows the permeation of hydrogen peroxide to the underlying electrodes 19 and 21, but that blocks the permeation of other low molecular weight molecules, such as acetaminophen, ascorbic acid, uric acid, salicylic acid, and amino acids, which otherwise could contribute to the generation of an electrical current. The layer sometimes is known in the art as a nano-filter.

The backing film 29 of the inner layer 25 is a porous polyester, with a preferred thickness of about 10–15 microns, and the overlay film 31 is a porous polysulfone coated onto the backing film, with a preferred thickness of about 1–2 microns or less. The composite layer is robust and substantially less prone to handling difficulties than are prior interference-barrier layers of this kind.

The intermediate layer 27 of the multi-layer membrane 15 incorporates the enzyme glucose oxidase, which as mentioned above functions as a catalyst in the reaction between glucose, water and oxygen that reach the layer from the blood sample in the channel 17. The glucose oxidase is immobilized in the layer along with canine albumin, which is added during the formulation process so as to enhance the stability of the enzyme activity. The preferred weight ratio of glucose oxidase:albumin is 85:65. During manufacture of the membrane, a viscous solution containing the glucose oxidase and albumin in spread onto the inner layer 25 using a conventional spincoating apparatus. The resulting layer has a preferred thickness of about 1–2 microns.

One advantage of the incorporation of albumin into the intermediate layer 27 is that it provides a desired elasticity to the layer. This improves the membrane's handleability. In addition, the albumin renders the layer more resistant to damage from gamma radiation and electron-beam radiation, i.e., enables it to retain its enzyme activity after receiving such radiation. This radiation, at a level of about 1 to 10 megarads in the case of gamma radiation, is used to sterilize the electrode assembly, making it suitable for use in a system that assays undiluted whole blood drawn from a patient and that subsequently reinfuses the blood back into the patient. An example of such an assay system is disclosed in U.S. Pat. No. 5,165,406, issued Nov. 24, 1992, in the name of David K. Wong and entitled "Electrochemical Sensor Apparatus and Method."

Like the outer layer 23, the optional mechanical support layer 28 can be a track-etched, polycarbonate film. It can have a thickness in the range of 10–15 microns, and its pores can be 0.6 microns in size, with a density of $3 \times 10_7$ pores per square centimeter, thus providing a porosity of 1–2 percent. This optional layer provides mechanical strength for the multi-layer membrane 15, without adversely inhibiting the diffusion of glucose.

It should be appreciated from the foregoing description that the present invention provides an improved electrode assembly for use in assaying glucose in solution, e.g., in whole blood. The assembly includes a special multi-layer membrane that can be sterilized by gamma radiation without reducing the activity of its glucose oxidase enzyme, and it reliably controls the flux of glucose and oxygen from the solution so as to eliminate the adverse effects of any oxygen deficit that might be present.

Although the invention has been described in detail with reference only to the preferred embodiment, those skilled in the art will appreciate that various modifications can be made without departing from the invention. Accordingly, the invention is defined only by the following claims.

We claim:

1. An electrode assembly for use in assaying glucose in a solution, the electrode assembly comprising:
    a sensor electrode; and
    a membrane assembly overlaying the sensor electrode the membrane assembly including
        an outer, diffusion-barrier layer positioned to contact the solution, the outer layer having a substantially uniform thickness and having a distribution of pores of a specific density and of a size in the range of 0.0125 to 0.0200 microns.
        an inner, interference-barrier layer contacting a face of the sensor electrode and having a substantially uniform thickness, wherein the inner layer includes a relatively thick, porous backing film and a relatively thin, porous overlaying film that overlays the backing film, and
        an immobilized glucose oxidase layer interposed between the outer and inner layers and having a substantially uniform thickness,
    wherein the outer layer is configured to allow glucose and oxygen to diffuse through it to reach the glucose oxidase layer, where the glucose and oxygen react to form reaction products that include hydrogen peroxide,
    and wherein the inner layer is configured to have a permeability sufficient to pass hydrogen peroxide from the glucose oxidase layer to the face of the sensor electrode.

2. An electrode assembly as defined in claim 1, wherein the outer layer is configured to allow the diffusion of oxygen from the solution to a substantially greater degree than it allows the diffusion of glucose from the solution.

3. An electrode assembly as defined in claim 2, wherein the outer layer is configured to be at least about 400 times more permeable to oxygen than it is to glucose.

4. An electrode assembly as defined in claim 2, wherein the outer layer is formed of polycarbonate.

5. An electrode assembly as defined in claim 2, wherein the outer layer has a thickness of about 6 microns.

6. An electrode assembly as defined in claim 2, wherein the pores in the outer layer contribute about 0.003 percent to about 0.015 percent of the outer layer's total porosity.

7. An electrode assembly as defined in claim 1, wherein the pores of the outer layer have a substantially random distribution.

8. An electrode assembly as defined in claim 1, wherein the backing film of the inner layer is formed of polyester and the overlaying film of the inner layer is formed of polysulfone.

9. An electrode assembly as defined in claim 1, wherein the backing film and overlaying film of the inner layer have a combined thickness of about 15 microns.

10. An electrode assembly as defined in claim 1, wherein the immobilized glucose oxidase layer carries glucose oxidase and albumin, in prescribed relative proportions.

11. An electrode assembly as defined in claim 10, wherein the weight ratio of glucose oxidase:albumin is about 85:65.

12. An electrode assembly for use in assaying glucose in a solution, the electrode assembly comprising:
    a sensor electrode; and
    a membrane assembly overlaying the sensor electrode, the membrane assembly including
        an outer, diffusion-barrier layer positioned to contact the solution, the outer layer having a uniform thickness and a distribution of pores of a specific density and a specific size,
        an inner, interference-barrier layer contacting a face of the sensor electrode and including a relatively thick, porous backing film and a relatively thin, porous overlaying film that overlays the backing film, the two films together having a uniform thickness, and
        an immobilized glucose oxidase layer interposed between the outer and inner layers,
    wherein the outer layer is configured to allow glucose and oxygen to diffuse through it to reach the glucose oxidase layer, where the glucose and oxygen react to form reaction products that include hydrogen peroxide,
    and wherein the inner layer is configured to have a permeability sufficient to pass hydrogen peroxide from the glucose oxidase layer to the face of the sensor electrode.

13. An electrode assembly as defined in claim 12, wherein the backing film of the inner layer is formed of polyester and the overlaying film of the inner layer is formed of polysulfone.

14. An electrode assembly as defined in claim 12, wherein the backing film and overlaying film of the inner layer have a combined thickness of about 15 microns.

15. An electrode assembly as defined in claim 12, wherein the pores in the outer layer have a size in the range of 0.0125 to 0.0200 microns.

16. An electrode assembly as defined in claim 12, wherein the immobilized glucose oxidase layer carries glucose oxidase and albumin, in prescribed relative proportions.

17. An electrode assembly as defined in claim 16, wherein the weight ratio of glucose oxidase:albumin is about 85:65.

* * * * *